United States Patent
Nagamatsu et al.

(10) Patent No.: US 10,125,378 B2
(45) Date of Patent: Nov. 13, 2018

(54) ADDITIVE FOR BIOETHANOL FERMENTATION PROCESS AND METHOD FOR PRODUCING BIOETHANOL

(71) Applicant: SAN NOPCO LTD., Kyoto-shi, Kyoto (JP)

(72) Inventors: Hironori Nagamatsu, Kyoto (JP); Tsuyoshi Ando, Kyoto (JP)

(73) Assignee: SAN NOPCO LTD., Kyoto (JP)

( * ) Notice: Subject to any disclaimer, the term of this patent is extended or adjusted under 35 U.S.C. 154(b) by 0 days.

(21) Appl. No.: 15/527,132

(22) PCT Filed: Jan. 8, 2016

(86) PCT No.: PCT/JP2016/050455
§ 371 (c)(1),
(2) Date: May 16, 2017

(87) PCT Pub. No.: WO2016/132760
PCT Pub. Date: Aug. 25, 2016

(65) Prior Publication Data
US 2017/0349916 A1    Dec. 7, 2017

(30) Foreign Application Priority Data

Feb. 17, 2015 (JP) .................. 2015-028965

(51) Int. Cl.
*C12P 7/06* (2006.01)
*C12P 7/10* (2006.01)

(52) U.S. Cl.
CPC .............. *C12P 7/06* (2013.01); *C12P 7/10* (2013.01); *C12P 2203/00* (2013.01); *Y02E 50/16* (2013.01)

(58) Field of Classification Search
None
See application file for complete search history.

(56) References Cited

U.S. PATENT DOCUMENTS

| | | | | |
|---|---|---|---|---|
| 5,843,734 A * | 12/1998 | Shonaka | ............ | B01D 19/0404 |
| | | | | 435/106 |
| 2010/0197559 A1* | 8/2010 | Kotera | ............ | C07C 41/03 |
| | | | | 510/506 |
| 2011/0171707 A1* | 7/2011 | Holt | ............ | C12N 1/18 |
| | | | | 435/161 |
| 2012/0225465 A1* | 9/2012 | Pimentel | ............ | C12P 7/10 |
| | | | | 435/165 |
| 2014/0171670 A1* | 6/2014 | Jenkins | ............ | C11B 13/00 |
| | | | | 554/19 |
| 2016/0128986 A1* | 5/2016 | O'Neil | ............ | A61K 39/00 |
| | | | | 424/490 |
| 2017/0349916 A1* | 12/2017 | Nagamatsu | ............ | C12P 7/06 |

FOREIGN PATENT DOCUMENTS

| | | |
|---|---|---|
| JP | 2-35073 A | 2/1990 |
| JP | 2005-270890 A | 10/2005 |
| JP | 2008-297229 A | 12/2008 |
| JP | 2012-75429 A | 4/2012 |
| JP | 2014-83466 A | 5/2014 |
| WO | 1997/000942 A1 | 1/1997 |
| WO | 2015/025538 A1 | 2/2015 |

OTHER PUBLICATIONS

Notification of Transmittal of Translation of the Internationl Preliminary Report on Patentability dated Aug. 31, 2017, issued in PCT/JP2016/050455.
International Search Report dated Apr. 5, 2016, issued in counterpart International Application No. PCT/JP2016/050455 (2 pages).

* cited by examiner

*Primary Examiner* — Joseph D Anthony
(74) *Attorney, Agent, or Firm* — Westerman, Hattori, Daniels & Adrian, LLP

(57) ABSTRACT

There is provided an additive for a bioethanol fermentation process comprising a polyoxyalkylene compound (A) having a Griffin's HLB value in the range of 0 to 6, a polyoxyalkylene polyol (B) and a base oil (C) that is liquid at 25° C. The compound (A) is preferably a mixture of a compound represented by a general formula (1) and a compound represented by a general formula (2). In the formula, $R^1$ and $R^3$ represent alkyl or alkenyl, $R^2$ and $R^4$ represent a hydrogen atom or a monovalent organic group, AO represents oxyalkylene having a carbon number of 3 to 18, a reaction residue of glycidol, a reaction residue of an alkyl glycidyl ether or a reaction residue of an alkenyl glycidyl ether, EO represents oxyethylene, m and n are 1 to 100, and p is 3 to 10.

$$R^1O\text{-}(AO)_m\text{—}R^2 \qquad (1)$$

$$R^3O\text{-}(AO)_n\text{-}(EO)_p\text{—}R^4 \qquad (2)$$

8 Claims, No Drawings

ADDITIVE FOR BIOETHANOL FERMENTATION PROCESS AND METHOD FOR PRODUCING BIOETHANOL

TECHNICAL FIELD

The present invention relates to an additive for a bioethanol fermentation process and a method for producing bioethanol.

BACKGROUND ART

Bioethanol is produced by alcohol fermentation, using sugar cane, corn, lignocellulose and the like, as a raw material (Patent Document 1, Non-Patent Document 1).

PRIOR ART DOCUMENTS

Patent Documents

Patent Document 1: JP 2008-297229 A

Non-Patent Documents

Non-Patent Document 1: "Biseibutsu-ni-yoru-Kagakuhannou" (document for guidance, Science No. 240, for junior high school and high school, and school for the blind, the deaf and the handicapped, November, 2003, published by Kagoshima Prefectural Institute For Education Research)

DISCLOSURE OF THE INVENTION

Problems to be Solved by the Invention

In the method described in Non-Patent Document 1, when production is performed on a commercial scale, there is a problem that the production efficiency is low. In addition, even in the method (or device) described in Patent Document 1, there is a problem that the production efficiency is not enough.

An object of the present invention is to provide an additive that can solve the above problems (i.e., can improve the production efficiency of bioethanol).

Solutions to the Problems

The present inventors have intensively studied to attain the above object, and consequently arrived at the present invention.

More specifically, the gist of the characteristics of the additive for a bioethanol fermentation process of the present invention is to contain a polyoxyalkylene compound (A) having a Griffin's HLB value in the range of 0 to 6, a polyoxyalkylene polyol (B) and a base oil (C) that is liquid at 25° C.

The gist of the characteristics of the method for producing bioethanol of the present invention, in which at least one selected from the group consisting of saccharide raw materials, starch raw materials and wooden (or cellulose) raw materials is used as a raw material, is to include a fermentation step of fermenting the raw material by adding the additive for a bioethanol fermentation process to a fermentation liquid.

Advantages of the Invention

The additive for a bioethanol fermentation process of the present invention exhibits markedly excellent production efficiency in a bioethanol fermentation process.

Bioethanol can be produced with high production efficiency by the method for producing bioethanol of the present invention.

Mode for Carrying Out the Invention

Examples of the polyoxyalkylene compound (A) having a Griffin's HLB value in the range of 0 to 6 include a polyoxyalkylene compound (A1) represented by a general formula (1), a polyoxyalkylene compound (A2) represented by a general formula (2), and mixtures thereof.

$$R^1O\text{-}(AO)_m\text{-}R^2 \quad (1)$$

$$R^3O\text{-}(AO)_n\text{-}(EO)_p\text{-}R^4 \quad (2)$$

Griffin's HLB value is the value calculated by the Griffin method (for example, "Shin-Kaimenkasseizai-Nyumon" authored by Takehiko Fujimoto, published by Sanyo Chemical Industries, Ltd., pages 128 to 131, 1981; corresponded English version: New Introduction to Surface Active Agents, T. Fujimoto, Sanyo Chemical Industries, Ltd., pages 128 to 131). In the calculation, only oxyethylene groups are defined as hydrophilic groups, and the other portions are defined as hydrophobic groups. In addition, when the polyoxyalkylene compound (A) is a mixture composed of a plurality of types of polyoxyalkylene compounds, HLB does not indicate an average of the plurality of types of polyoxyalkylene compounds, but the respective values of the polyoxyalkylene compounds.

$R^1$ and $R^3$ represent an alkyl group or alkenyl group having a carbon number of 4 to 28, $R^2$ and $R^4$ represent a hydrogen atom or a monovalent organic group having a carbon number of 1 to 24, AO represents an oxyalkylene group having a carbon number of 3 to 18, a reaction residue of glycidol, a reaction residue of an alkyl glycidyl ether having a carbon number 4 to 21 or a reaction residue of an alkenyl glycidyl ether having a carbon number of 5 to 21, EO represents an oxyethylene group, m and n are an integer of 1 to 100, and p is an integer of 3 to 10.

Examples of the alkyl group or alkenyl group having a carbon number of 4 to 28 ($R^1$, $R^3$) include an alkyl group (R) and an alkenyl group (R').

Examples of the alkyl group (R) include butyl, t-butyl, octyl, 2-ethylhexyl dodecyl, tetradecyl, hexadecyl, octadecyl, and the like.

Examples of the alkenyl group (R') include butenyl, octenyl, isooctenyl, dodecenyl, octadecenyl, and the like.

Among them, alkyl groups (R) are preferred from the viewpoint of production efficiency.

Among the hydrogen atom or the monovalent organic group having a carbon number of 1 to 24 ($R^2$, $R^4$), examples of the monovalent organic group having a carbon number of 1 to 24 include alkyl groups (R), alkenyl groups (R'), acyl groups (—COR), aroyl groups (—COR'), N-alkylcarbamoyl groups (—CONHR), N-alkenylcarbamoyl groups (—CONHR'), alkylcarbonylamino groups (—NHCOR), alkenylcarbonylamino groups (—NHCOR'), alkylcarboxyamino groups (alkylcarbamate groups, —NHCOOR), and alkenylcarboxyamino groups (alkenylcarbamate groups, —NHCOOR'). Among chemical formulae written in the parentheses, R and R' correspond to the alkyl group (R) and alkenyl group (R'), respectively.

Among the hydrogen atom or the monovalent organic groups having a carbon number of 1 to 24 ($R^2$, $R^4$), a hydrogen atom or alkyl group (R) is preferred from the viewpoint of production efficiency.

Among the oxyalkylene group having a carbon number of 3 to 18, the reaction residue of glycidol, the reaction residue of the alkyl glycidyl ether having a carbon number 4 to 21 or the reaction residue of the alkenyl glycidyl ether having a carbon number of 5 to 21 (AO), examples of the oxyalkylene group having a carbon number of 3 to 18 include oxypropylene, oxybutylene, oxyisobutylene, oxy-1,2-decylene, oxy-1,12-dodecylene, oxy-1,2-dodecylene, oxy-1,2-octadecylene, and the like.

In addition, among (AO), examples of the reaction residue of the alkyl glycidyl ether having a carbon number of 4 to 21 include a reaction residue of methyl glycidyl ether, ethyl glycidyl ether, butyl glycidyl ether, 2-ethyl hexyl glycidyl ether, dodecyl glycidyl ether, octadecyl glycidyl ether, or the like.

Moreover, among (AO), examples of the reaction residue of the alkenyl glycidyl ether having a carbon number of 5 to 21 include a reaction residue of vinyl glycidyl ether, butenyl glycidyl ether, 2-ethyl hexenyl glycidyl ether, dodecenyl glycidyl ether, octadecenyl glycidyl ether, or the like.

m and n are an integer of 1 to 100, preferably an integer of 2 to 75, and further preferably an integer of 3 to 60.

p is an integer of 3 to 10, preferably an integer of 4 to 8, and further preferably an integer of 4 to 6.

When the polyoxyalkylene compound (A) is a mixture of the polyoxyalkylene compound (A1) represented by the general formula (1) and the polyoxyalkylene compound (A2) represented by the general formula (2), the content of the polyoxyalkylene compound (A1) represented by the general formula (1) is preferably 0.1 to 90% by weight, further preferably 1 to 85% by weight, and particularly preferably 5 to 80% by weight, based on the weight of the polyoxyalkylene compound (A). In this case, the content of the polyoxyalkylene compound (A2) represented by the general formula (2) is preferably 10 to 99.9% by weight, further preferably 15 to 99% by weight, and particularly preferably 20 to 95% by weight, based on the weight of the polyoxyalkylene compound (A).

Examples of the polyoxyalkylene polyol (B) preferably include at least one selected from the group consisting of a polyoxypropylene polyol (B1) represented by a general formula (3), a polyoxyethylene polyoxypropylene polyol (B2) represented by a general formula (4), a polyoxyethylene polyoxypropylene polyol (B3) represented by a general formula (5), a polyoxyethylene polyoxypropylene polyol (B4) represented by a general formula (6) and a polyoxyethylene polyoxypropylene polyol (B5) represented by a general formula (7).

$$R^5-[-(PO)_q-H]_r \quad (3)$$

$$R^6-[-(EO)_s-(PO)_q-H]_r \quad (4)$$

$$R^7-[-(PO)_q-(EO)_s-H]_r \quad (5)$$

$$R^8-[-(EO)_q-(PO)_q-(EO)_t-H]_r \quad (6)$$

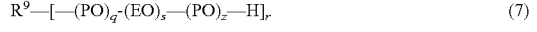

$$R^9-[-(PO)_q-(EO)_s-(PO)_z-H]_r \quad (7)$$

$R^5$, $R^6$, $R^7$, $R^8$ and $R^9$ are a hydroxyl group or a reaction residue of an active hydrogen compound having a carbon number of 1 to 25, PO is an oxypropylene group, EO is an oxyethylene group, q, s, t and z are an integer of 1 to 100, and r is an integer of 1 to 10. The oxyethylene group and the oxypropylene group in the general formulae (4), (5), (6) and (7) are bound in a block form.

Among $R^5$, $R^6$, $R^7$, $R^8$ and $R^9$, the reaction residue of an active hydrogen compound having a carbon number of 1 to 25 means a reaction residue formed by excluding an active hydrogen from the active hydrogen compound having a carbon number of 1 to 25.

Examples of the active hydrogen-containing compound having a carbon number of 1 to 25 include compounds containing at least one hydroxyl group (—OH), imino group (—NH—), amino group (—NH$_2$) and/or carboxyl group (—COOH), that is, an alcohol, an amide, an amine, a carboxylic acid, a hydroxycarboxylic acid, and an aminocarboxylic acid.

Examples of the alcohol include monools (methanol butanol, stearyl alcohol, oleyl alcohol, isostearyl alcohol, etc.), polyols (ethylene glycol, propylene glycol, glycerin, diglycerin, tetraglycerin, trimethylol propane, pentaerythritol, dipentaerythritol, dihydroxyacetone, fructose, glucose, mannose, galactose, sucrose, lactose, trehalose, etc.), and the like.

Examples of the amide include monoamides (formic acid amide, propionic acid amide, stearylamide, etc.), polyamides (malonic acid diamide, ethylene bis-octylamide, etc.), and the like.

Examples of the amine include monoamines (dimethylamine, ethylamine, aniline, stearylamine, etc.), polyamines (ethylenediamine, diethylenetriamine, triethylenetetramine, etc.), and the like.

Examples of the carboxylic acid include monocarboxylic acids (acetic acid, stearic acid, oleic acid, benzoic acid, etc.), polycarboxylic acids (maleic acid, hexanedioic acid, etc.), and the like.

Examples of the hydroxycarboxylic acid include hydroxyacetic acid, tartaric acid, malic acid, 12-hydroxystearic acid, and the like.

Examples of the aminocarboxylic acid include glycine, 4-aminobutyric acid, 6-aminohexanoic acid, 12-aminolauric acid, and the like.

q, s, t and z are an integer of 1 to 100, preferably an integer of 2 to 75, and further preferably an integer of 3 to 60.

r is an integer of 1 to 10, preferably an integer of 1 to 7, and further preferably an integer of 1 to 5.

Among them, the polyoxypropylene polyol (B1) represented by the general formula (3) and the polyoxyethylene polyoxypropylene polyol (B4) represented by the general formula (6) are preferred, from the viewpoint of production efficiency.

Examples of the base oil (C) that is liquid at 25° C. preferably include at least one selected from the group consisting of a hydrocarbon oil (C1), a glycerin fatty acid ester (C2), a monoalcohol fatty acid ester (C3) and a silicone (C4).

As the hydrocarbon oil (C1), one refined by appropriately combining distillation under reduced pressure, oil deasphalting, solvent extraction, hydrocracking, solvent dewaxing, sulfuric acid washing, clay refining, hydrorefining, and the like can be used, and examples of the trade name thereof include COSMO PURESPIN G, COSMO PURESPIN E, COSMO SP-10, COSMO SP-32, and COSMO SC22 (all manufactured by COSMO OIL Co., Ltd.; "COSMO" and "PURESPIN" are registered trademarks of the company), MC Oil P-22 and S-10S (all manufactured by Idemitsu Kosan Co., Ltd.), STANOL 40 (manufactured by Exxon Mobil Corporation) and the like.

Examples of the glycerin fatty acid ester (C2) include esters of fatty acids having a carbon number of 6 to 22 or mixtures thereof with glycerin, and specifically include vegetable oils (rapeseed oil, soybean oil, palm oil, coconut oil, olive oil, and the like), medium chain fatty acid glycerides (examples of the trade name thereof include PANACET 875, available from NOF Corporation; "PANACET" is a registered trademark of this company), fish oils and the like.

Examples of the monoalcohol fatty acid esters (C3) include esters of fatty acids having a carbon number of 6 to 22 or mixtures thereof with monoalcohols having a carbon number of 1 to 22, the esters being liquid at 25° C., and specifically include methyl oleate, butyl oleate, methyl isostearate and the like.

Examples of the silicones (C4) include silicone oil and modified silicone oil

Examples of the silicone oil include polydimethylsiloxanes having a kinematic viscosity of 10 to 10000 (mm²/s, at 25° C.) and also include cyclopolymethylpolysiloxane (cyclooctamethyltetrasiloxane etc,) and the like.

Examples of the modified silicone include ones resulting from substituting some of the methyl groups of the abovementioned polydimethylsiloxane or cyclopolymethylpolysiloxane with an alkyl group having a carbon number of 2 to 6, an alkoxyl group having a carbon number of 2 to 4, a phenyl group, a hydrogen atom, a halogen (chlorine, bromine, or the like) atom, an alkoxypolyoxyalkylene oxypropyl group (the alkoxy has a carbon number of 1 to 6; the alkylene has a carbon number of 2 to 3; the degree of polymerization is 2 to 50; and the weight of the oxyethylene group is less than 20% by weight of the overall weight of the oxyalkylene group), an alkoxypolyaxyalkylene group (the alkoxy has a carbon number of 1 to 6; the alkylene has a carbon number of 2 to 3; the degree of polymerization is 2 to 50; and the weight of the oxyethylene group is less than 20% by weight of the overall weight of the oxyalkylene group) and/or an aminoalkyl group having a carbon number of 2 to 6.

Among the base oil (C) that is liquid at 25° C., the hydrocarbon oil (C1), the glycerin fatty acid ester (C2) and the silicone (C4) are preferred, and combinations of some or all of them are more preferred.

The content of the polyoxyalkylene compound (A) is preferably 1 to 69% by weight, further preferably 3 to 54% by weight, and particularly preferably 6 to 40% by weight, based on the total weight of the polyoxyalkylene compound (A), the polyoxyalkylene polyol (B) and the base oil (C) that is liquid at 25° C. The content of the polyoxyalkylene polyol (B) is preferably 1 to 63% by weight, further preferably 2 to 51% by weight, and particularly preferably 6 to 40% by weight, based on the total weight of the polyoxyalkylene compound (A), the polyoxyalkylene polyol (B) and the base oil (C) that is liquid at 25° C. The content of the base oil (C) that is liquid at 25° C. is preferably 30 to 90% by weight, further preferably 40 to 80% by weight, and particularly preferably 50 to 70% by weight, based on the total weight of the polyoxyalkylene compound (A), the polyoxyalkylene polyol (B) and the base oil (C) that is liquid at 25° C.

The additive for a bioethanol fermentation process of the present invention may contain at least one hydrophobic compound (D) selected from the group consisting of hydrophobic silica (D1), hydrophobic amide (D2), hydrophobic wax (D3), hydrophobic synthetic resin (D4) and hydrophobic metallic soap (D5).

Examples of the hydrophobic silica (D1) include hydrophobic silica prepared by hydrophobizing a silica powder with a hydrophobizing agent.

Exemplary trade names of the commercially available hydrophobic silica include Nipsil SS-10, SS-40, 88-50, and SS-100 (Tosoh Silica Corporation, "Nipsil" is a registered trademark of Tosoh Silica Corporation), AEROSIL R972, RX200, and RY200 (Nippon Aerosil Co., Ltd., "AEROSIL" is a registered trademark of Evonik Degussa GmbH), SIPERNAT D10, D13, and D17 (Degussa Japan Co., Ltd., "SIPERNAT" is a registered trademark of Evonik Degussa GmbH), TS-530, TS-610, and TS-720 (Cabot Carbon Corporation), AEROSIL R202, R805, and R812 (Degussa Japan Co., Ltd.), REOLOSIL MT-10, DM-10, and DM-20S (Tokuyama Corporation, "REOLOSIL" is a registered trademark of this company), and SYLOPHOBIC 100, 702, 505, and 603 (Fuji Silysia Chemical Ltd., "SYLOPHOBIC" is a registered trademark of this company).

The hydrophobic amide (D2) includes a reaction product (fatty acid diamide) of an alkylenediamine having a carbon number of 1 to 6 or an alkenylenediamine having a carbon number of 2 to 6 with a fatty acid having a carbon number of 10 to 22 and/or a reaction product (fatty acid monoamide) of an alkylamine having a carbon number of 1 to 22, an alkenylamine having a carbon number of 2 to 6, or ammonia with a fatty acid having a carbon number 10 to 22.

Examples of the fatty acid diamide include ethylene bis-stearylamide, ethylene bis-palmitylamide, ethylene bis-myristylamide, ethylene bis-laurylamide, ethylene bis-oleylamide, propylene bis-stearylamide, propylene bis-palmitylamide, propylene bis-myristylamide, propylene bis-laurylamide, propylene bis-oleylamide, butylene bis-stearylamide, butylene bis-palmitylamide, butylene bis-myristylamide, butylene bis-laurylamide, butylene bis-oleylamide, methylene bis-laurylamide, methylene bis-stearylamide, hexamethylene bis-stearylamide and the like.

Examples of the fatty acid monoamide include N-stearyl stearylamide, oleic acid amide, erucic acid amide, stearylamide and the like.

Among them, the fatty acid diamide is preferred. More preferred are ethylene bis-stearylamide, ethylene bis-palmitylamide, ethylene bis-laurylamide, methylene bis-stearylamide, and hexamethylene bis-stearylamide, and particularly preferred are ethylene bis-stearylamide, ethylene bis-palmitylamide, and ethylene bis-myristylamide. These amides may be in the form of a mixture of two or more members, and in the case of a mixture, it is preferred that any of the aforementioned preferable members be contained as a primary component.

The primary component means a component that is contained in at least 40% by weight based on the weight of the hydrophobic amide (D2), preferably in 50% by weight or more, more preferably in 60% by weight or more, particularly preferably in 70% by weight or more, and most preferably in 80% by weight or more.

Examples of auxiliary components (components contained in addition to the primary component) in the hydrophobic amide (D2) include an unreacted amine and an unreacted carboxylic acid as well as amides other than those within the aforementioned preferred range. The content (% by weight) of the auxiliary components is preferably less than 60, more preferably less than 50, particularly preferably less than 40, more preferably less than 30, and most preferably less than 20 based on the weight of the hydrophobic amide (D2).

Examples of the hydrophobic wax (D3) include a petroleum wax, a synthetic wax and a vegetable wax.

Examples of the petroleum wax include waxes that can be dispersed in the base oil (C) and that are by-produced from petroleum refining, and specifically include microcrystalline wax, paraffin wax and the like.

Examples of the synthetic wax include waxes that can be dispersed in the base oil (C) and that can be prepared by chemical synthesis, and specifically include Fischer-Tropsch wax, polyethylene wax, oxidized polyethylene wax, alcohol-modified wax, maleic acid-modified oxidized polyethylene wax and the like.

Examples of the vegetable wax include waxes that can be dispersed in the base oil (C) and that are extracted from plants, and specifically include carnauba wax, Japan wax and the like.

Examples of the hydrophobic synthetic resin (D4) include a synthetic resin (D41) containing an ethylenically unsaturated monomer (dm1) as a constitutional unit or a synthetic resin (D42) containing a monomer for polycondensation and polyaddition (dm2) as a constitutional unit.

Examples of the ethylenically unsaturated monomer (dm1) include publicly known ethylenically unsaturated monomers and the like, and there can be used (meth)acrylic acid; alkyl esters (having a carbon number of 1 to 22) of (meth)acrylic acid {methyl (meth)acrylate, ethyl (meth) acrylate, butyl (meth)acrylate, (2-ethylhexyl) (meth)acrylate, stearyl (meth)acrylate, behenyl (meth)acrylate, and the like}; (meth)acrylates of adducts of alkylene oxide (having a carbon number of 2 to 4) to alcohols having a carbon number of 1 to 18 {(meth)acrylates of adducts of 30 mol propylene oxide to methanol, (meth)acrylates of adducts of 30 mol propylene oxide to 2-ethylhexanol, (meth)acrylates of adducts of 30 mol ethylene oxide to stearylalcohol, and the like}; (meth)acrylonitrile; styrenes (styrene, methylstyrene, and hydroxystyrene); diaminoethyl (meth)acrylate; polyfunctional vinyl monomers (divinylbenzene, ethylene di(meth)acrylate, trimethylolpropane tri(meth)acrylate, and polyethylene glycol (degree of polymerization: 14) di(meth) acrylate); allyl alcohol; adducts of alkylene oxides (having a carbon number of 2 to 4) to allyl alcohol {adducts of 2 mol propylene oxide to allyl alcohol, and the like}; 2-buten-1-ol; (2-hydroxyethyl) (meth)acrylate; adducts of alkylene oxides (having a carbon number of 2 to 4) to (2-hydroxyethyl) (meth)acrylate {an adduct of 4 mol propylene oxide to (2-hydroxyethyl) (meth)acrylate, and the like}: butadiene; isoprene; vinyl chloride; vinylidene chloride; vinyl acetate; and the like.

Although these may be used alone or two or more of them may be used together, it is preferred to use at least one monomer having a polyoxyalkylene group {e.g., (meth) acrylates of adducts of alkylene oxide (having a carbon number of 2 to 4) to alcohols having a carbon number of 1 to 18; polyethylene glycol (degree of polymerization: 14) di(meth)acrylate; adducts of alkylene oxide (having a carbon number of 2 to 4) to allyl alcohol; and adducts of alkylene oxides (having a carbon number of 2 to 4) to (2-hydroxyethyl) (meth)acrylate}.

(Meth)acrylic acid represents acrylic acid and/or methacrylic acid, (meth)acrylonitrile represents acrylonitrile and/ or methacrylonitrile, and (meth)acrylate represents acrylate and/or methacrylate.

The synthetic resin (D41) containing an ethylenically unsaturated monomer (dm1) as a constitutional unit can be obtained by polymerization by a publicly known method. These may be reacted in the base oil (C) that is liquid at 25° C. and then used directly, or alternatively the synthetic resin prepared beforehand by performing reaction and the base oil (C) that is liquid at 25° C. may be mixed.

Examples of the monomer for polycondensation and polyaddition (dm2) include publicly known monomers for polycondensation and polyaddition, and specifically include a polyisocyanate (dm21), a polyamine (dm22), a polyol (dm23), and a polycarboxylic acid (dm24).

Examples of the polyisocyanate (dm21) include diisocyanates having a carbon number of 8 to 16 {hexamethylene diisocyanate, tolylene diisocyanate, isophorone diisocyanate, 4-4'-methylene bis(cyclohexylisocyanate), and the like}, their modified products (trimethylolpropane adducts of diisocyanate, biuret condensates, isocyanurate condensates, and the like) and the like.

Examples of the polyamine (dm22) include polyamines having a carbon number of 1 to 6, and specifically include urea, melamine, ethylenediamine, hexamethylenediamine, diethylenetriamine, triethylenetetramine and the like.

Examples of the polyol (dm23) include polyhydric alcohols having a carbon number of 2 to 6 {ethylene glycol, propylene glycol butylene glycol, glycerin, diglycerin, pentaerythritol, and the like}; adducts prepared by adding 1 to 50 mol of alkylene oxide having a carbon number of 2 to 4, per one hydroxyl group, to such polyhydric alcohols {ethylene oxide adducts, propylene oxide adducts, butylene oxide adducts, ethylene oxide/propylene oxide block adducts, or propylene oxide/butylene oxide block adducts of polyhydric alcohols, and the like}; and the like.

Examples of the polycarboxylic acid (dm24) include polycarboxylic acids having a carbon number of 4 to 14, and specifically include terephthalic acid, isophthalic acid, naphthalene dicarboxylic acid, biphenyldicarboxylic acid, oxalic acid, succinic acid, adipic acid, sebacic acid, fumaric acid, maleic acid, itaconic acid, dimer acid and the like.

Examples of the synthetic resin (D42) containing a monomer for polycondensation and polyaddition (dm2) as a constitutional unit include polyureas, polyurethanes, and polyesters containing the above-mentioned monomer as a constitutional unit, and the synthetic resin can be produced by performing reaction by a publicly known method. These may be reacted in the base oil (C) that is liquid at 25° C. and then used directly, or alternatively the synthetic resin prepared beforehand by performing reaction and the base oil (C) that is liquid at 25° C. may be mixed.

The synthetic resin (D4) can be obtained from the market, and for example, the following commercial products can be used.

ULTIFLOW FS-7301 (Sanyo Chemical Industries, Ltd., a dispersion of an ethylenically unsaturated monomer-copolymerized product in a polyether, "ULTIFLOW" is a registered trademarks of this company), DAIMICBEAZ UCN-8070CM Clear (Dainichiseika Color & Chemicals Mfg. Co., Ltd., polyurethane beads, "DAINAMICBEAZ" is a registered trademarks of this company), and TAFTIC F-120 and F-167 (Toyobo Co., Ltd., a dispersion of an ethylenically unsaturated monomer-copolymerized product in water; "TAFTIC" is a registered trademark of this company)

Examples of the metallic soap (D5) include salts of fatty acids having a carbon number of 12 to 22 with metals (alkaline earth metal, aluminum, manganese, cobalt, lead, chromium, copper, iron, nickel, and the like), and specifically include aluminum stearate, calcium stearate, zinc laurate, magnesium behenate and the like.

In the case of containing the hydrophobic compound (D), the content (% by weight) of the hydrophobic compound (D) is preferably 2 to 30, more preferably 4 to 25, and particularly preferably 5 to 20 based on the total weight of the polyoxyalkylene compound (A), the polyoxyalkylene polyol (B) and the base oil (C) that is liquid at 25° C.

The additive for a bioethanol fermentation process of the present invention may additionally contain water, a thickener, a dispersant, an antiseptic, a film forming conditioner, an antifreezing agent and/or a solvent.

Examples of the thickener include xanthan gum, locust bean gum, guar gum, carrageenan, alginic acid and a salt thereof tragacanth gum, magnesium aluminum silicate, bentonite, synthetic hydrous silicic acid, a synthetic polymer type thickener containing a carboxyl group (exemplary trade names include SN-Thickener 636 and SN-Thickener 641;

SAN NOPCO Ltd), an association type thickener containing a polyoxyethylene chain (exemplary trade names include SN-Thickener 625N and SN-Thickener 665T; SAN NOPCO Ltd.) and the like.

Examples of the dispersant include a polyacrylic acid (salt), a partial saponification type polyvinyl alcohol, a sulfated polyvinyl alcohol and the like.

Examples of the antiseptic include a publicly known antiseptic (Dictionary of Antibacterial and Antifungal Agents, 1st Ed., pp. 1-32, published by The Society for Antibacterial and Antifungal Agents, Japan, 1986, etc.) and specifically include formalin, 5-chloro-2-methyl-4-isothiazolin-3-one and the like.

Examples of the trade name of film forming conditioner include TEXANOL (manufactured by Eastman Chemical Company; "TEXANOL" is a registered trademark of YOSHIMURA OIL CHEMICAL Co., Ltd.) and the like.

Examples of the antifreezing agent include ethylene glycol, propylene glycol, glycerin and the like.

Examples of the solvent include a publicly known solvent (Solvent Handbook, pp. 143-881, published by Kodansha, 1976, etc) and specifically include butylcellosolve, propylene glycol monopropyl ether, 1-butanol and the like.

The additive for a bioethanol fermentation process of the present invention can be obtained by applying a known production method.

The polyoxyalkylene compound (A) and the polyoxyalkylene polyol (B) can be produced by a known alkylene oxide addition reaction and an etherification reaction. Then, the polyoxyalkylene compound (A), the polyoxyalkylene polyol (B) and the base oil (C) that is liquid at 25° C. are uniformly mixed to obtain the additive for a bioethanol fermentation process of the present invention.

In the case of containing the hydrophobic compound (D), water, the thickener, the dispersant, the antiseptic, the film forming conditioner, the antifreezing agent and/or a solvent in the additive for a bioethanol fermentation process of the present invention, these in addition to the polyoxyalkylene compound (A), the polyoxyalkylene polyol (B) and the base oil (C) that is liquid at 25° C. are uniformly mixed by a known method to obtain the additive of the present invention.

The temperature and time of the uniform mixing are not particularly limited so long as the compounds can be uniformly mixed, but are preferably 5 to 60° C. and 10 minutes to 5 hours. Also, there is no particular restriction on the mixing device for uniformly mixing the compounds, and a blade type stirrer, a line mixer or the like can be used.

As a raw material which can be used in the method for producing bioethanol of the present invention, at least one selected from the group consisting of saccharide raw materials, starch raw materials and wooden (or cellulose) raw materials can be used.

The saccharide raw materials are food resources containing much saccharide, and examples include sugar cane, molasses, sugar beet, and the like.

The starch raw materials are food resources containing much starch, and examples include corn, sorghum, potato, sweet potato, wheat, and the like.

The wooden (or cellulose) raw materials are inedible food resources containing much cellulose, and examples include woods, waste building materials, and the like. As the wood, in addition to coniferous trees (pine, fir, hemlock, spruce, larch, radiata pine, etc.) and broadleaf trees (eucalyptus, poplar, beech, maple, birch, etc.), kenaf, paper bush, paper mulberry, Diplomorpha, mulberry, Manila hemp, reed, bamboo and the like are included. These woods may be thinnings, lumber waste, driftwood and pruned branches, and may contain the branches of woods, roots and leaves. The waste building materials include waste wooden building materials, waste wooden pallets, waste wooden packing materials, and the like.

As the method for producing bioethanol of the present invention, known methods can be applied, and examples include saccharification pretreatment process, saccharification process, and ethanol fermentation process.

In the ethanol fermentation process, a microorganism and the additive for a bioethanol fermentation process are added to a fermentation liquid, and then fermented.

The microorganism is preferably at least one selected from the group consisting of a bacteria and a yeast. Examples of such microorganism include genetically modified *Escherichia coli* and the like. The genetically modified *E. coli* means one in which the enzyme gene necessary for the conversion to ethanol etc. is introduced into *Escherichia coli* that does not have the enzyme gene by genetic engineering technology and fermentation for ethanol is enabled. Examples of the yeast include a publicly known yeast and specifically include *Saccharomyces cerevisiae, Schizosaccharomyces pombe* and the like. These microorganism may be a dried fungus body (dry yeast and the like).

The amount of the additive for a bioethanol fermentation process added is not particularly limited, and is preferably about 0.0001 to 5% by weight, based on the weight of the fermentation liquid.

The fermentation liquid passed through the ethanol fermentation process is subjected to a separation process of separating the produced ethanol. As a method for separating ethanol, a known method such as distillation method and pervaporation membrane method can be used. Ethanol obtained by separation may be used as it is, or may be used after purification by a known method such as distillation.

EXAMPLES

Hereinbelow, the present invention will be described further in detail with reference to examples, but the present invention is not limited thereto. Unless otherwise indicated, parts mean parts by weight, and % means % by weight.

The Polyoxyalkylene compound (A), the polyoxyalkylene polyol (B), the base oil (C) that is liquid at 25° C. and the hydrophobic compound (D) used Examples, are shown below.

<Polyoxyalkylene Compound (A)>

Polyoxyalkylene compounds (a11 to a16, a21 to a27) synthesized by known methods are shown in Tables 1 to 2. In the tables, PO represents oxypropylene, EO represents oxyethylene, and BO represents oxybutylene (the same is applied also hereinafter).

TABLE 1

$R^1O$—$(AO)_m$—$R^2$ (1)

| | $R^1$ | $(AO)_m$ | $R^2$ | HLB |
|---|---|---|---|---|
| a11 | Butyl | $(PO)_{60}$ | Lignoceryl | 0 |
| a12 | Cetyl | $(PO)_{14}$ | Hydrogen atom | 0 |
| a13 | Montanyl | $(BO)_1$ | Methyl | 0 |
| a14 | Myristyl | $(PO)_{14}$ | Hydrogen atom | 0 |
| a15 | Butyl | $(PO)_{100}$ | Hydrogen atom | 0 |
| a16 | Cetyl | $(PO)_3$ | Hydrogen atom | 0 |

TABLE 2

$R^3O\text{—}(AO)_n\text{—}(EO)_P\text{—}R^4$ (2)

|     | $R^3$    | $(AO)_n$      | p  | $R^4$         | HLB |
|-----|----------|---------------|----|---------------|-----|
| a21 | Montanyl | $(PO)_{10}$   | 10 | Ethyl         | 6   |
| a22 | Cetyl    | $(PO)_{14}$   | 6  | Hydrogen atom | 4   |
| a23 | Butyl    | $(PO)_{100}$  | 3  | Methyl        | 0.4 |
| a24 | Myristyl | $(PO)_{14}$   | 4  | Hydrogen atom | 2.9 |
| a25 | Cetyl    | $(BO)_1$      | 3  | Lignoceryl    | 3.3 |
| a26 | Myristyl | $(PO)_3$      | 3  | Hydrogen atom | 5.1 |
| a27 | Butyl    | $(PO)_{60}$   | 7  | Hydrogen atom | 1.6 |

<Polyoxyalkylene Polyol (B)>

Polyoxyalkylene polyols (b31 to b37, b41 to b43, b51 to b53, b61 to b67, and b71 to b73) synthesized by known methods are shown in Tables 1 to 3.

TABLE 3

|     | Structural formula |
|-----|--------------------|
| b31 | HO—[—$(PO)_{30}$—H]$_1$ |
| b32 | HO—[—$(PO)_{34}$—H]$_1$ |
| b33 | (Glyceryl)-[—$(PO)_{16}$—H]$_3$ |
| b34 | (Glyceryl)-[—$(PO)_2$—H]$_3$ |
| b35 | (Stearyl)-[—$(PO)_{75}$—H]$_1$ |
| b36 | $C_{17}H_{35}COO$—[—$(PO)_{15}$—H]$_1$ |
| b37 | $CH_3CH_2N$—[—$(PO)_3$—H]$_2$ |
| b41 | (Methyl)-[—$(EO)_{60}$—$(PO)_{70}$—H]$_1$ |
| b42 | HO—[—$(EO)_3$—$(PO)_{60}$—H]$_1$ |
| b43 | $C_2H_5C(\text{=}O)N$—[—$(EO)_7$—$(PO)_3$—H]$_2$ |
| b51 | (Lignoceryl)-[—$(PO)_3$—$(EO)_3$—H]$_1$ |
| b52 | HO—[—$(PO)_{60}$—$(EO)_{60}$—H]$_1$ |
| b53 | $CH_3CH_2N$—[—$(PO)_3$—$(EO)_3$—H]$_2$ |
| b61 | HO—[—$(EO)_8$—$(PO)_{37}$—$(EO)_8$—H]$_1$ |
| b62 | HO—[—$(EO)_3$—$(PO)_{37}$—$(EO)_3$—H]$_1$ |
| b63 | HO—[—$(EO)_{60}$—$(PO)_{37}$—$(EO)_{60}$—H]$_1$ |
| b64 | (Glyceryl)-[—$(EO)_7$—$(PO)_3$—$(EO)_3$—H]$_3$ |
| b65 | (Stearyl)-[—$(EO)_7$—$(PO)_{60}$—$(EO)_3$—H]$_1$ |
| b66 | $C_{17}H_{35}COO$—[—$(EO)_2$—$(PO)_8$—$(EO)_2$—H]$_1$ |
| b67 | $CH_3CH_2N$—[—$(EO)_3$—$(PO)_5$—$(EO)_3$—H]$_2$ |
| b71 | $CH_3CH_2N$—[—$(PO)_{50}$—$(EO)_8$—$(PO)_3$—H]$_2$ |
| b72 | HO—[—$(PO)_3$—$(EO)_3$—$(PO)_{60}$—H]$_1$ |
| b73 | (Stearyl)-[—$(PO)_3$—$(EO)_{60}$—$(PO)_3$—H]$_2$ |

<Base Oil (C) that is Liquid at 25° C.>

Base oil (c11) that is liquid at 25° C.: Mineral oil, COSMO PURESPIN G, manufactured by Cosmo oil lubricants Co., Ltd.

Base oil (c12) that is liquid at 25° C.: Mineral oil, COSMO PURESPIN E, manufactured by Cosmo oil lubricants Co., Ltd.

Base oil (c21) that is liquid at 25° C.: Edible rapeseed oil, manufactured by Nikko seiyu Co., Ltd.

Base oil (c31) that is liquid at 25° C.: Methyl oleate, EXCEPARL M-OL, manufactured by Kao Corporation, "EXCEPARL" is a registered trademark of this company Base oil (c41) that is liquid at 25° C.: Dimethyl silicone oil (kinematic viscosity 50 (mm$^2$/s, at 25° C.)), KF-96L-5CS, manufactured by Shin-Etsu Chemical Co., Ltd.

Base oil (c42) that is liquid at 25° C.: Dimethyl silicone oil, (kinematic viscosity 3000 (mm$^2$/s, 25 C)), KF-96-3,000CS, manufactured by Shin-Etsu Chemical Co., Ltd.

Base oil (c43) that is liquid at 25° C.: Silicone compound in which, of the methyl groups of dimethylsilicone (number average molecular weight: 1800), four methyl groups per a molecule in average were substituted with a polyoxypropylene (25 mol) oxypropyl group <Hydrophobic Compound (D)>

Hydrophobic compound (d1): Hydrophobic silica, Nipsil SS-100, manufactured by Tosoh Silica Corporation Hydrophobic compound (d12): Hydrophobic silica, AEROSIL R972, manufactured by Nippon Aerosil Co., Ltd.

Hydrophobic compound (d13): Hydrophobic silica, SIPERNAT D10, manufactured by Degussa Japan Co., Ltd.

Hydrophobic compound (d14): Hydrophobic silica, Nipsil G-0251, manufactured by Tosoh Silica Corporation Hydrophobic compound (d21): Ethylene bisoleylamide, ALFLOW AD-281F, manufactured by NOF Corporation Hydrophobic compound (d23): Stearylamide, Amide AP-1, manufactured by Nippon Kasei Chemical Co., Ltd.

Hydrophobic compound (d24): Hexamethylene bisstearylamide, ITOHWAX J-630, manufactured by Itoh Oil Chemicals Co., Ltd.

Hydrophobic compound (d31): Micrcrystalline wax, Hi-Mic-2095, manufactured by Nippon Seiro Co., Ltd.

Hydrophobic compound (d32): Fischer-Tropsch wax, FT-105, manufactured by Nippon Seiro Co., Ltd.

Hydrophobic compound (d33): Oxidized polyethylene wax, Epolene E-10, manufactured by Eastman Chemical Company Hydrophobic compound (d34): Alcohol-modified wax, OX-3405, manufactured by Nippon Seiro Co., Ltd.

Hydrophobic compound (d35): Carnauba wax, Carnauba Wax No. 1, manufactured by S. Kato & Co.

Hydrophobic compound (d41): Synthetic resin, product prepared in accordance with Example 1 of JP-A-2009-7506 {copolymer having as constitutional units (styrene)/(acrylonitrile)/(divinylbenzene)/(reactive dispersant obtained by jointing a propylene oxide adduct of glycerol and 2-hydroxymethyl methacrylate with tolylene diisocyanate (TDI))/(polyoxyalkylene ether prepared by adding propylene oxide to allyl alcohol) (particle diameter: 0.7 μm)}

Hydrophobic compound (d51): Aluminum stearate, SA-1500, manufactured by Sakai Chemical Industry Co., Ltd.

Example 1

The polyoxyalkylene compound (a11) [6.3 parts] and the polyoxyalkylene compound (a21) [0.7 parts] were uniformly mixed by stirring at 30° C. for 30 minutes by a blade-type stirrer, then the polyoxyalkylene polyol (b31) [63 parts] and the base oil (c11) that is liquid at 25° C. [30 parts] were added to this mixture, and the mixture was uniformly mixed by stirring at 30° C. for 1 hour to obtain an additive (1) for a bioethanol fermentation process of the present invention.

Examples 2 to 27

The same procedures were carried out as in Example 1, except for changing the polyoxyalkylene compound (a11) [6.3 parts], the polyoxyalkylene compound (a21) [0.7 parts], the polyoxyalkylene polyol (b31) [63 parts] and the base oil (c11) that is liquid at 25° C. [30 parts] to the polyoxyalkylene compounds, polyoxyalkylene polyols and base oils that is liquid at 25° C. (the type and the number of parts) shown in Table 4 to obtain the additives (2) to (27) for a bioethanol fermentation process of the present invention. As well, in Examples 2 and 6 to 19, hydrophobic compounds (the type and the number of parts) shown in Table 4 is added together with polyoxyalkylene polyols and base oils that is liquid at 25° C.

TABLE 4

| | | Polyoxyalkylene compound (A) | | | | Polyoxyalkylene polyol (B) | | Base oil (C) that is liquid at 25° C. | | Hydrophobic compound (D) | |
| | | (A1) | | (A2) | | | | | | | |
| | | Type | Number of parts | Type | Number of parts | Type | Number of parts | Type | Number of parts | Type | Number of parts |
|---|---|---|---|---|---|---|---|---|---|---|---|
| Examples | 1 | a11 | 6.3 | a21 | 0.7 | b31 | 63 | c11 | 30 | — | — |
| | 2 | a12 | 17.5 | a22 | 17.5 | b32 | 15 | c12 | 50 | d12 | 5 |
| | 3 | a13 | 0.63 | a23 | 62.37 | b33 | 7 | c21 | 30 | — | — |
| | 4 | a11 | 35 | — | — | b41 | 15 | c31 | 50 | — | — |
| | 5 | — | — | a21 | 21 | b51 | 9 | c41 | 70 | — | — |
| | 6 | a12 | 10.5 | a22 | 10.5 | b61 | 9 | c42 | 70 | d13 | 2 |
| | 7 | a13 | 3.5 | a23 | 3.5 | b71 | 3 | c43 | 90 | d14 | 20 |
| | 8 | a14 | 3.5 | a24 | 3.5 | b32 | 3 | c41 | 90 | d21 | 30 |
| | 9 | a15 | 1.5 | a25 | 3 | b32 | 25.5 | c11 | 70 | d22 | 5 |
| | 10 | a16 | 17.85 | a26 | 3.15 | b33 | 9 | c12 | 70 | d23 | 5 |
| | 11 | a11 | 17.5 | a27 | 17.5 | b33 | 21 | c11 | 50 | d24 | 5 |
| | 12 | a11 | 17.5 | a21 | 17.5 | b34 | 15 | c12 | 50 | d31 | 5 |
| | 13 | a12 | 17.5 | a22 | 17.5 | b35 | 15 | c11 | 50 | d32 | 5 |
| | 14 | a13 | 17.5 | a23 | 17.5 | b36 | 15 | c12 | 50 | d33 | 5 |
| | 15 | a14 | 17.5 | a24 | 17.5 | b37 | 15 | c11 | 50 | d34 | 5 |
| | 16 | a11 | 17.5 | a21 | 17.5 | b42 | 15 | c12 | 50 | d35 | 5 |
| | 17 | a12 | 17.5 | a22 | 17.5 | b43 | 15 | c11 | 50 | d41 | 5 |
| | 18 | a13 | 17.5 | a23 | 17.5 | b52 | 15 | c12 | 50 | d51 | 5 |
| | 19 | a14 | 17.5 | a24 | 17.5 | b53 | 15 | c11 | 50 | d11 | 4 |
| | 20 | a11 | 62.1 | a21 | 6.9 | b64 | 1 | c12 | 30 | — | — |
| | 21 | a12 | 0.07 | a22 | 68.93 | b65 | 1 | c11 | 30 | — | — |
| | 22 | a13 | 0.8 | a23 | 0.2 | b66 | 63 | c12 | 36 | — | — |
| | 23 | a14 | 0.05 | a24 | 0.95 | b67 | 9 | c11 | 90 | — | — |
| | 24 | a11 | 32 | a21 | 8 | b72 | 10 | c12 | 50 | — | — |
| | 25 | a12 | 2 | a22 | 38 | b73 | 6 | c11 | 54 | — | — |
| | 26 | a13 | 4.8 | a23 | 1.2 | b62 | 40 | c12 | 54 | — | — |
| | 27 | a14 | 0.3 | a24 | 5.7 | b63 | 24 | c11 | 70 | — | — |

Using the additives for a bioethanol fermentation process obtained in Examples 1 to 27, the production efficiency test was carried out as follows, and the results are shown in Table 5. As a blank, the result of testing without using the additive for a bioethanol fermentation process is also shown in Table 5.

<Production Efficiency Test>

Since the production efficiency of bioethanol fermentation in laboratory levels cannot be compared, the following accelerated test was performed.

100 mL of a bioethanol fermentation liquid created by diluting 200 parts of commercially available sugar cane molasses (purchased from MARUKYO NOSAN CO., LTD) with 800 parts of ion-exchanged water and 1 g of a dry yeast (SUPER CAMELLIA, a dried fungus body of *Saccharomyces cerevisiae*, purchased from Nisshin seifun Group Inc., "SUPER CAMELLIA" is a registered trademark of Nisshin seifun Group Inc.) were put in a glass graduated cylinder with an inner diameter of 50 mm×height of 350 mm, 30 μL of a measurement sample (additive for a bioethanol fermentation process) was added with a microsyringe, and a diffuser stone was inserted into the bottom of the liquid, then carbon dioxide gas was bubbled at 500 mL/min. The volume (mL) of the bioethanol fermentation liquid after 10 minutes was read, and the production efficiency (%) was calculated from the following equation. The smaller the value, the size of the fermenter to be used in the production can be reduced, and the production efficiency is improved.

Production efficiency(9)=(Volume of bioethanol fermentation liquid after 10 minutes)/100

TABLE 5

| | | HLB of polyoxyalkylene compound (A) | Production efficiency (%) |
|---|---|---|---|
| Example | 1 | 0 and 6 | 180 |
| | 2 | 0 and 4 | 150 |
| | 3 | 0 and 0.4 | 190 |
| | 4 | 0 | 330 |
| | 5 | 6 | 260 |
| | 6 | 0 and 4 | 180 |
| | 7 | 0 and 0.4 | 160 |
| | 8 | 0 and 2.9 | 190 |
| | 9 | 0 and 3.3 | 190 |
| | 10 | 0 and 5.1 | 200 |
| | 11 | 0 and 1.6 | 180 |
| | 12 | 0 and 6 | 190 |
| | 13 | 0 and 4 | 170 |
| | 14 | 0 and 0.4 | 150 |
| | 15 | 0 and 2.9 | 180 |
| | 16 | 0 and 6 | 160 |
| | 17 | 0 and 4 | 150 |
| | 18 | 0 and 0.4 | 170 |
| | 19 | 0 and 2.9 | 190 |
| | 20 | 0 and 6 | 240 |
| | 21 | 0 and 4 | 230 |
| | 22 | 0 and 0.4 | 200 |
| | 23 | 0 and 2.9 | 210 |
| | 24 | 0 and 6 | 170 |
| | 25 | 0 and 4 | 180 |
| | 26 | 0 and 0.4 | 160 |
| | 27 | 0 and 2.9 | 150 |
| Blank | | — | 600< |

The additive for a bioethanol fermentation process of the present invention had extremely good production efficiency, as compared to those not using the additive for a bioethanol fermentation process (blank).

INDUSTRIAL APPLICABILITY

The additive for a bioethanol fermentation process of the present invention is suitable as an additive for improving the production efficiency of bioethanol.

The invention claimed is:

1. An additive for a bioethanol fermentation process comprising a polyoxyalkylene compound (A) having a Griffin's HLB value in the range of 0 to 6, a polyoxyalkylene polyol (B) and a base oil (C) that is liquid at 25° C.,
    wherein the content of the polyoxyalkylene compound (A) is 1 to 69% by weight, the content of the polyoxyalkylene polyol (B) is 1 to 63% by weight and the content of the base oil (C) that is liquid at 25° C. is 30 to 90% by weight, based on the total weight of the polyoxyalkylene compound (A), the polyoxyalkylene polyol (B) and the base oil (C) that is liquid at 25° C.

2. The additive according to claim 1, wherein the polyoxyalkylene compound (A) is a mixture of a polyoxyalkylene compound (A1) represented by a general formula (1) and a polyoxyalkylene compound (A2) represented by a general formula (2);

  (1)

  (2)

wherein $R^1$ and $R^3$ represent an alkyl group or alkenyl group having a carbon number of 4 to 28, $R^2$ and $R^4$ represent a hydrogen atom or a monovalent organic group having a carbon number of 1 to 24, AO represents an oxyalkylene group having a carbon number of 3 to 18, a reaction residue of glycidol, a reaction residue of an alkyl glycidyl ether having a carbon number of 4 to 21 or a reaction residue of alkenyl glycidyl ether having a carbon number of 5 to 21, EO represents an oxyethylene group, m and n are an integer of 1 to 100, and p is an integer of 3 to 10.

3. The additive according to claim 1, wherein the polyoxyalkylene polyol (B) is at least one selected from the group consisting of a polyoxypropylene polyol (B1) represented by a general formula (3), a polyoxyethylene polyoxypropylene polyol (B2) represented by a general formula (4), a polyoxyethylene polyoxypropylene polyol (B3) represented by a general formula (5), a polyoxyethylene polyoxypropylene polyol (B4) represented by a general formula (6), and a polyoxyethylene polyoxypropylene polyol (B5) represented by a general formula (7);

  (3)

  (4)

  (5)

  (6)

  (7)

wherein $R^5$, $R^6$, $R^7$, $R^8$ and $R^9$ are a hydroxyl group or a reaction residue of an active hydrogen compound having a carbon number of 1 to 25, PO is an oxypropylene group, EO is an oxyethylene group, q, s, t and z are an integer of 1 to 100, and r is an integer of 1 to 10; and the oxyethylene group and the oxypropylene group in the general formulae (4), (5), (6) and (7) are bound in a block form.

4. The additive according to claim 1, wherein the base oil (C) that is liquid at 25° C. is at least one selected from the group consisting of a hydrocarbon oil (C1), a glycerin fatty acid ester (C2), a monoalcohol fatty acid ester (C3) and a silicone (C4).

5. The additive according to claim 1 further comprising at least one hydrophobic compound (D) selected from the group consisting of hydrophobic silica (D1), hydrophobic amide (D2), hydrophobic wax (D3), hydrophobic synthetic resin (D4) and hydrophobic metallic soap (D5).

6. The additive according to claim 2, wherein the content of the polyoxyalkylene compound (A1) represented by the general formula (1) is 0.1 to 90% by weight, and the content of the polyoxyalkylene compound (A2) represented by the general formula (2) is 10 to 99.9% by weight, based on the weight of the polyoxyalkylene compound (A).

7. The additive according to claim 5, wherein the content of the hydrophobic compound (D) is 2 to 30% by weight based on the total weight of the polyoxyalkylene compound (A), the polyoxyalkylene polyol (B) and the base oil (C) that is liquid at 25° C.

8. A method for producing bioethanol in which at least one selected from the group consisting of saccharide raw materials, starch raw materials and wooden (or cellulose) raw materials is used as a raw material, the method comprising:
    a fermentation step of fermenting the raw material by adding the additive as defined in claim 1 to a fermentation liquid.

* * * * *